United States Patent

Remes

[11] Patent Number: 5,881,731
[45] Date of Patent: Mar. 16, 1999

[54] DEVICE FOR TREATMENT OF INCONTINENCE OF URINE

[76] Inventor: Arto Remes, Visakuja 4 F 18, Kuopio, Finland, 70420

[21] Appl. No.: 873,461

[22] Filed: Jun. 12, 1997

Related U.S. Application Data

[63] Continuation of Ser. No. 701,130, Aug. 21, 1996, abandoned, which is a continuation of PCT/FI95/00087 Feb. 21, 1995.

[30] Foreign Application Priority Data

Feb. 21, 1994 [FI] Finland .................................... 940799

[51] Int. Cl.⁶ ........................................................ A61F 5/48
[52] U.S. Cl. ............................................ 128/885; 607/138
[58] Field of Search ........................................ 128/846, 885, 128/886, 738, 778, 733; 607/39, 138

[56] References Cited

U.S. PATENT DOCUMENTS

| | | | |
|---|---|---|---|
| 4,909,263 | 3/1990 | Norris | 607/138 |
| 4,953,563 | 9/1990 | Kaiser et al. | |
| 5,154,177 | 10/1992 | Eisman et al. | |
| 5,423,329 | 6/1995 | Ergas | 607/138 |
| 5,483,832 | 1/1996 | Pauser | 128/778 |

FOREIGN PATENT DOCUMENTS

| | | |
|---|---|---|
| 4038853 | 6/1991 | Germany . |
| 2119516 | 11/1983 | United Kingdom . |
| WO92/20283 | 11/1992 | WIPO . |
| WO93/17619 | 9/1993 | WIPO . |
| WO94/15667 | 7/1994 | WIPO . |

Primary Examiner—Michael A. Brown
Attorney, Agent, or Firm—Pillsbury Madison & Sutro LLP

[57] ABSTRACT

The invention relates to a device for treating incontinence, which device includes a frame part (1) and a, at least partially tubular, sensor part (2) fastened at an angle in relation to the frame part, having sensors (3) on its sides for measuring the function of the pelvic floor muscles. According to the invention: the sensor part is detachably attached to the frame part (1), which makes it exchangeable regarding to every patient; the sensors (3) are placed on the sides of the sensor-part-tube, on both sides of the center of the side; and the sensors (3) are electrodes which are arranged to measure the muscle activity of the pelvic floor muscles with the help of the electrical signal produced by them.

10 Claims, 3 Drawing Sheets

DEVICE FOR TREATMENT OF INCONTINENCE OF URINE

This is a continuation of application Ser. No. 08/701,130, filed on Aug. 21, 1996, which was abandoned upon the filing hereof, and which is a continuation of PCT/FI95/00087, filed Feb. 21, 1995.

The invention relates to a device for treating incontinence, which device includes a frame part and a, at least partially tubular, sensor part fastened at an angle in relation to the frame part, having sensors on its sides for measuring the function of the pelvic floor muscles.

Incontinence means reduction of the ability to restrain urine. The main reason to the problem is the weakening of the pelvic floor muscles and the reduction of their ability to be activated. This may be influenced by a lot of different reasons, for example overweight, psychological reasons and as one reason, the reduction of the restraining ability caused by the delivery of children. It is essential when treating incontinence to restore the muscle strength and the muscle control of the patients pelvic floor muscles. This may be realized through practice or electrical stimulation of the muscles.

These days different kinds of devices exist with which it is possible to exercise the pelvic floor muscles and/or measure their activity. The device is placed in the vagina and when the muscles are contracted the condition of the muscles is elucidated with the help of the data transmitted by the sensors. By repeating the contracting exercises the muscle strength is grown to a level where the problem to hold the urine disappears. With the training made possible with the devices it may be possible to avoid surgery.

Several problems are connected with the known devices. The devices are generally intended for use only in research and laboratory conditions and are not possible to use at home. The devices are often staff-shaped and their use is troublesome. In addition, some devices have a thickening at the end of the staffs which is an inconvenience to the measurements in standing and squatting position. When using some devices it is not possible to get them completely clean in spite of the sterilization or exchange of the sensor part, but secretions from the body may transfer from the sensor part to the frame part and stay in cavities in the device. Another problem is the conveniency to handle and the safety to use the device. A disadvantage is also that the device is not easy to adjust to the user.

Devices also exist where a pressure sensor is placed inside a flexible tube which is placed into the vagina. This kind of measurement with pressure is not accurate enough, since it is possible to create pressure in the vagina by squeezing the feet or the muscles in the abdomen or the seat. A disadvantage when using pressure sensors is that it is not possible to discover a situation where the muscles on one side are functioning worse than the muscles on the other side.

The object of the invention is to bring forward a device for treating incontinence with which disadvantages connected to present devices are removed. The object of the invention is especially to bring forward a device which is easy to use both at home and in laboratory conditions and which is safe, reliable and hygienic. Further, the object of the invention is to bring forward a device which is adjustable for different users or which the user may adjust to different values in different phases of the treatment.

The object of the invention is achieved with a device characterized by that described in the claims.

According to the invention the sensor part is detachably attached to the frame part, the sensors are placed on the sides of the sensor-part-tube, on both sides of the center of the side, and the sensors are electrodes which are arranged to measure the muscle activity of the pelvic floor muscles with the help of the electrical signal produced by them. A sensor part according to the invention is a so called disposable part which is exchanged after each patient so that the device is hygienic and safe. When using the device at home it is possible, when the same patient is using the device, to continuously use the sensor part several times in a row. In this case it shall be carefully cleaned after use. The frame part is only exchanged if it is broken. An electronic case is placed inside the frame part, inside which adjustment and functioning organs are placed.

The measurement taking place with the apparatus is preferably based on electromyographic measurement (EMG). The muscle activation of the pelvic floor expressed with a rms-EMG-signal is from a few micro volts to about 50–80 $\mu V$. The electrode plate pairs functioning as sensors register the sum-potential of the contracting muscle and thus the signal accurately describes the activation capacity of the pelvic floor muscles on both sides. The measurement results are collected separately from each side.

A device with a frame part according to the invention is accurately placed in its position in the vagina by placing it in such a position that the frame part extends forward. In this case the sensors are in the desired way at the muscles to be examined or exercised. An additional advantage is that the frame part is spacious enough and can be equipped with the necessary measurement and control electronics and possibly with a displaying device. Still, the device is so small that it can be placed under the trousers.

In the advantageous embodiment of the invention the sensor part is an integrated moulded part. The sensors are situated on the side surface of the tubular part during the moulding, forming a part of the construction. When the sensor part is moulded as an integrated part no secretions from the body may enter the sensor part and therethrough continue to the frame part. Thus the device is sufficiently hygienic all the time.

In the second embodiment of the invention a cover belongs to the lower part of the sensor part. The lower surface of the cover is placed on the upper surface of the frame part. The cover protects the frame part so that the frame part does not come into contact with the secretions from the body. The cover is placed at an angle compared with the other part of the sensor part.

The contact connections between the sensors and the frame part are advantageously placed at the frame part. In this way the risk of contamination is small.

In an advantageous additional embodiment of the invention the tube of the sensor part is converging essentially over its whole length 1°–5° against the tip. The tube does not press against the user too much and does not cause pain when using the device. The device may be used in a lying-down, a standing and a squatting position.

In an advantageous embodiment of the invention the sensors are placed on the sides of the tube on both sides of the center of the side symmetrically and at about an 50°–70° angle compared with each other seen from the center of the tube. When the device is accurately placed in its position with the help of the invention, reliable knowledge is acquired of the muscles on both sides separately.

In the following the invention is explained in more detail by referring to the accompanying drawings where FIG. 1 shows an embodiment of a device according to the invention seen at an angle from below when the sensor part and the frame part are separated from each other.

A device according to the figures includes a frame part 1 and a sensor part 2 detachably attachable to the frame part. A tubular part belongs to the sensor part. The sensors 3 are fastened on the sides of the tubular part. The sensors are ordinary measuring-sensors suitable for the purpose and their number may vary in different embodiments. The sensors are sufficiently long so that they are suitable for different women and are placed at the pelvic floor muscles when the device is in its place. At the lower part of the tubular part are formed a widening-part extending away from and downwards from the tubular part, and a protective edge extending downwards from the widening-part. The widening-part and the protective edge form together the cover 4. The cover is arranged at a blunt angle compared with the rest of the sensor part. The tube is converging about 1°–5° against the tip, which makes it easy to place into the vagina. The material in the sensor is known material which resists disinfection and cleaning.

Figure 4:
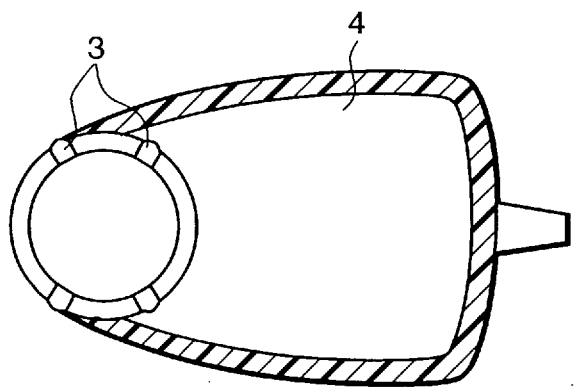
FIG. 4 shows a section A—A according to FIG. 3.

The sensors 3 are placed on the sides of the tube on both sides of the center in the manner as shown in FIG. 4. In this embodiment they are at about an 60° angle compared with each other. The sensor part is moulded from homogenous material in such a way that the sensors are first placed in the mould and the plastic part is moulded around them so that the sensors are integrated in the construction so that it does not have any cracks or slits.

The tube in the sensor part has in this embodiment a circular cross-section but the cross-section may be elliptical in other embodiments.

Figure 3:
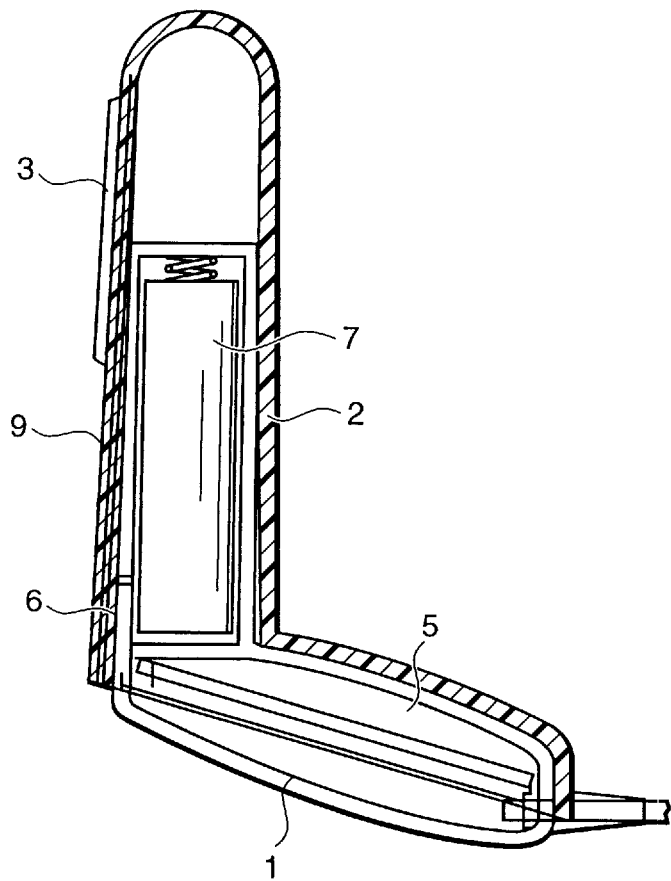
FIG. 3 shows a section of a device according to FIG. 2.

In accordance with FIG. 3 contacting parts 9 are formed at the sides of the tube, with which parts 9 the information given by the sensors is transferred to the frame part 1. An electronic case 5 is placed inside the frame part, which case includes printed circuits and electronic parts for adjustment and use of the device. The frame part is essentially flat, and in the shown embodiments a signalling device and a display unit 8 are placed on its lower surface.

Figure 1:
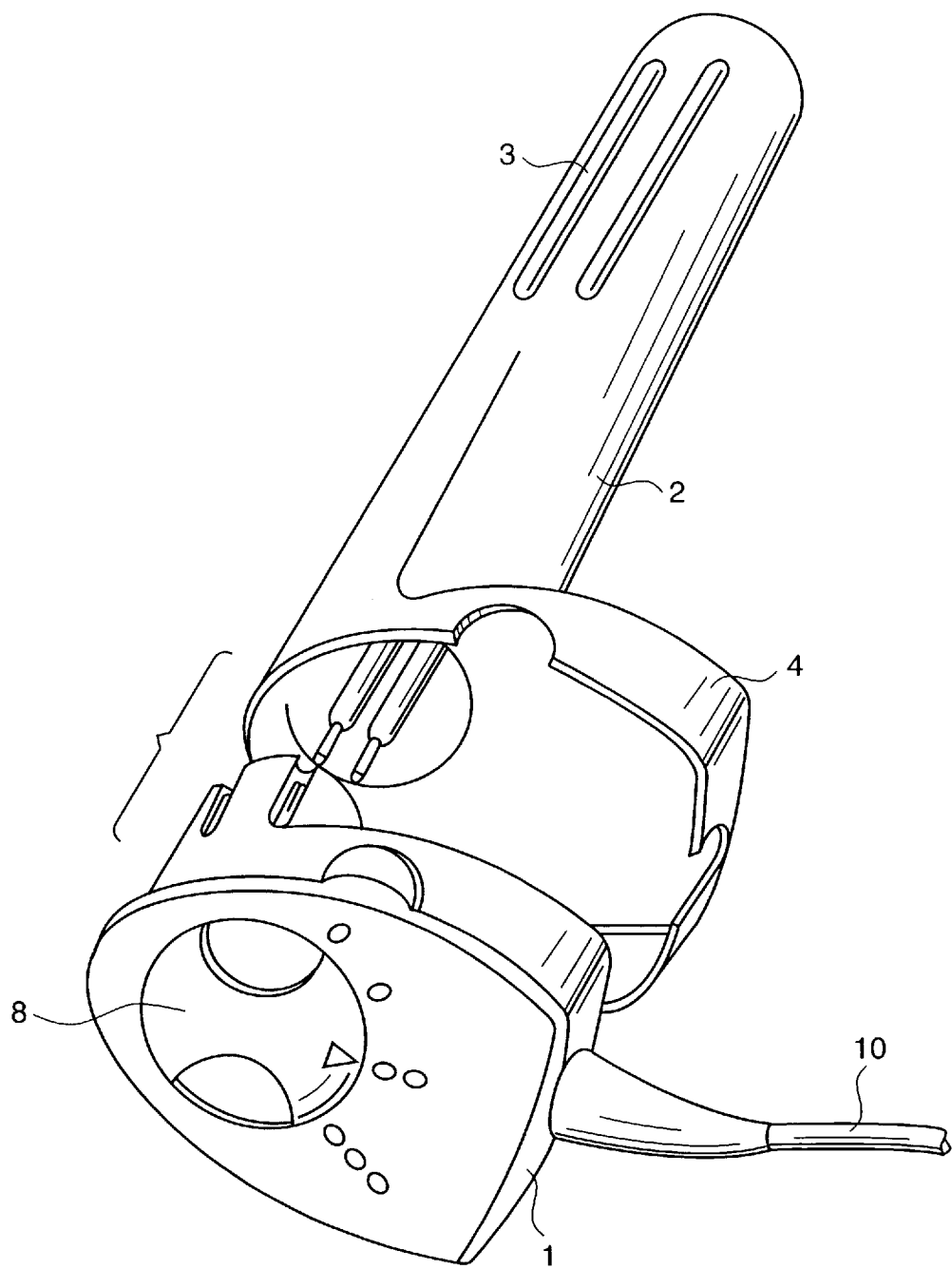
Figure 2:
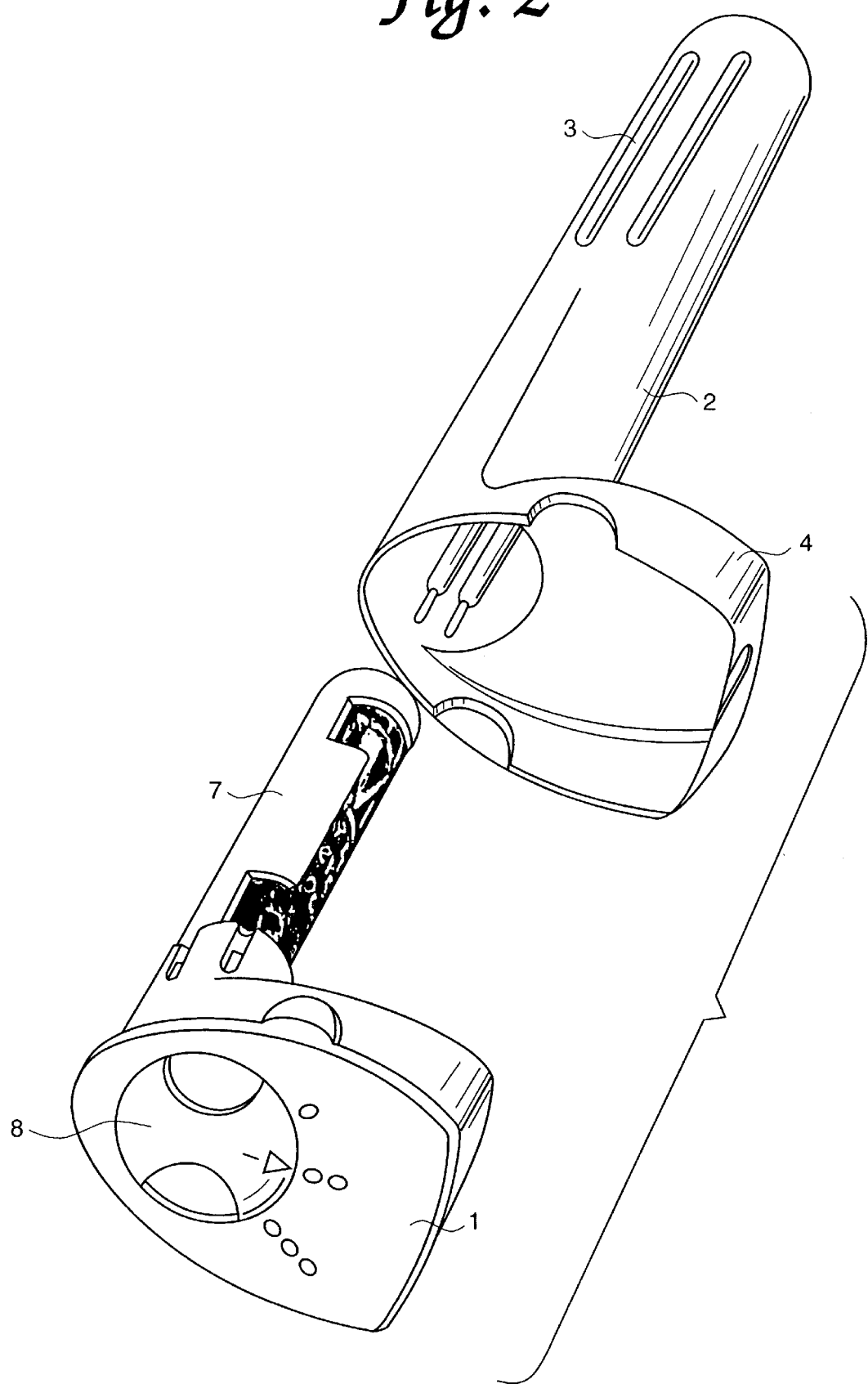
FIG. 2 shows another embodiment of a device according to the invention seen at an angle from below when the sensorpart and the frame part are separated from each other.

In an embodiment according to FIG. 1 the device is connected with a cable 10 to a using apparatus which provides it with energy. The display unit and the signalling device may in this case be placed in the frame part or in a separate display unit. In an embodiment according to FIG. 2 the energy needed to use the device is provided by an accumulator 7 or a battery which is fastened to the frame part in such a way that it reaches into the tube in the frame part. When using an accumulator or a battery the device may be used in home conditions or in a laboratory without an outer energy source. In one embodiment a transmitter unit is connected to the frame part for sending a message without using a cable, and a separate display unit and/or a signalling device which may for example be a device that is to be placed on the wrist belongs to the device.

The signalling device 8 is arranged to be programmed in a manner known in itself to a desired value and to be calibrated to a pre set value. The device has in this case pre set standard levels, for example the levels shown in FIGS. 1 and 2 marked with one and two circles. In the third position it is possible to set suitable individual practice levels for the whole device. The standard levels may then be changed when the practice is progressing and when trying to reach a new practice level.

One embodiment of the invention is a device intended for men. On men the measurement is done in the anal orifice into which the pelvic floor muscles reach. The functional principle of the device stays the same, but the outer dimensions of the sensor is different from those on the models intended for women.

In an additional embodiment of the invention an alternative for stimulation is incorporated into the device. In this case, necessary devices for emitting electrical pulses to the pelvic floor muscles are attached to the device in a known manner.

The invention is not limited to the shown advantageous embodiments. It may vary within the scope of the inventive idea as stated in the claims.

I claim:

1. Device for treating incontinence, comprising:

a frame part, and a sensor part which is at least partially a tubular part and which is positioned at an blunt angle in relation to the frame part, said sensor part having sensors for measuring a function of pelvic floor muscles, said sensors being electrodes which are arranged to measure muscle activity of pelvic floor muscles with the help of an electrical signal produced by said muscles, wherein said sensor part is detachably attached to the frame part so as to be exchangeable with regard to every patient, and said tubular part has sides and said sensors are disposed symmetrically opposite each other on said sides of the tubular part, on both sides of a center of each said side for collecting measurement results separately from both sides of the pelvic floor muscle, such that the positions of the sensors with respect to the pelvic floor muscles are ascertainable by referencing the frame part in a predetermined direction.

2. A device according to claim 1, wherein the sensor part is an integrated moulded part and the sensors are integrally moulded on a side surface of said tubular part.

3. A device according to claim 1 or 2, including a cover for a lower part of the sensor part, a lower surface of the cover being disposed on an upper surface of the frame part.

4. A device according to claim 2, wherein said tubular part converges essentially over its whole length about 1°–5° toward a tip.

5. A device according to claim 1, includes contact connections between the sensors and the frame part, said contact connections being placed at the frame part.

6. A device according to claim 2, wherein the sensors are placed at about a 50°–70° angle compared to each other.

7. A device according to claim 1, including a power device fastened on the frame and placed inside the sensor part.

8. A device according to claim 1, including at least one of a signalling device and a display unit placed on a lower surface of the frame part.

9. A device according to claim 8, wherein said one of a signalling device and display unit are programmed to a desired value and calibrated to a preset value.

10. A device according to claim 1, including an electronic case disposed inside the frame part, which case includes adjustment and functioning organs of the device.

* * * * *